United States Patent [19]
Kroeger et al.

[11] Patent Number: 4,876,512
[45] Date of Patent: Oct. 24, 1989

[54] METHOD FOR RAPIDLY DETERMINING THE SWELLING-CLAY CONTENT IN SHALES AND SHALY SANDSTONE FORMATIONS BY HIGH-FREQUENCY DIELECTRIC CONSTANT MEASUREMENTS

[75] Inventors: Michael K. Kroeger; John M. Longo; Ronald P. Steiger, all of Houston; Peter K. Leung, Sugar Land, all of Tex.

[73] Assignee: Exxon Production Research Company, Houston, Tex.

[21] Appl. No.: 175,081

[22] Filed: Mar. 30, 1988

[51] Int. Cl.$^4$ .......................... G01V 3/06; G01V 3/12
[52] U.S. Cl. ........................................ 324/376; 73/153
[58] Field of Search ....................... 324/376, 377, 341; 73/151, 152, 153

[56] References Cited

U.S. PATENT DOCUMENTS

| | | | |
|---|---|---|---|
| 2,802,172 | 8/1957 | Mueller et al. | 324/376 |
| 3,302,101 | 1/1967 | Glanville | 324/376 |
| 3,617,868 | 11/1971 | Beitel et al. | 324/376 |
| 3,982,177 | 9/1976 | Walker et al. | 324/376 |
| 4,410,052 | 10/1983 | Mamadzhanov et al. | 324/351 X |
| 4,608,859 | 9/1986 | Rockley | 73/153 |
| 4,644,283 | 2/1987 | Vinegar et al. | 324/376 |
| 4,652,829 | 3/1987 | Safinya | 324/341 X |
| 4,654,598 | 3/1987 | Arulanandan et al. | 324/354 |
| 4,734,649 | 3/1988 | Barnaby | 324/376 |
| 4,769,606 | 9/1988 | Vinegar et al. | 324/376 X |

OTHER PUBLICATIONS

Van Olphen, H., "An Introduction to Clay Colloid Chemistry", Wiley-Interscience, New York, 1977, Chapter 5.
Theng, B. K. G., "The Chemistry of Clay-Organic Reactions", John Wiley & Sons, New York, 1974, Chapter 3.
Jaynes, W. F. and Bigham, J. M., "Multiple Cation-Exchange Capacity Measurements on Standard Clays Using a Commercial Mechanical Extractor", Clays and Minerals, 1986, vol. 34, No. 1, pp. 93-98.
Raythatha, R. and Sen, P. N., "Dielectric Properties of Clay Suspensions in the MHz to GHz Range", Journal of Colloid and Interface Science, Feb. 1986, vol. 109, No. 2, pp. 301-309.
Shen, L. C., "Problems in Dielectric-Constant Logging and Possible Routes to Their Solutions", The Log Analyst, 1985, Nov.-Dec., pp. 14-25.
Wharton, R. P., et al., "Electromagnetic Propagation Logging: Advances in Technique and Interpretation", 55th Ann. Fall Tech. Conf., Dallas, Texas, Sep. 21-24, 1980, SPE Paper 9267.
Lockhardt, N. C., "Electrical Properties and the Surface Characteristics and Structure of Clays", Journal of Colloid and Interface Science, 1980, vol. 74, No. 2, pp. 509-519.
Weiler, R. A. and Chaussidon, J., "Surface Conductivity and Dielectric Properties of Montmorillonite Gels", Clay and Minerals, 1968, vol. 16, pp. 147-155.
Fernando, M. J., Burau, R. G., and Arulanandan, K., "A New Approach to Determination of Cation Exchange Capacity", Soil Sci. Soc. Am. Journal, vol. 41, 1977.
Ariathurai, R. and Arulanandan, K., "An Electrical Method to Measure In-Situ Sediment Densities", Workshop on Cohesive Sediment Dynamics with Special Reference to Physical Processes in Estuaries, Tampa, Florida, Nov. 12-14, 1984.

Primary Examiner—Reinhard J. Eisenzopf
Assistant Examiner—Warren S. Edmonds
Attorney, Agent, or Firm—Raul R. Montes

[57] ABSTRACT

A method for determining at wellsites the swelling-clay content of shales and shaly sandstones earth formations whereby a sample of the formation is washed with a fluid having a water activity substantially less than that of water, which fluid may contain a soluble cation, and measurements of the sample's dielectric constant are made at a preselected frequency for subsequent comparison to calibration curves, thereby obtaining a measurement of the welling-clay content of the formation. The determinations of the swelling-clay content may be performed at different levels depending on the nature of the samples.

43 Claims, 2 Drawing Sheets

METHOD FOR RAPIDLY DETERMINING THE SWELLING-CLAY CONTENT IN SHALES AND SHALY SANDSTONE FORMATIONS BY HIGH-FREQUENCY DIELECTRIC CONSTANT MEASUREMENTS

FIELD OF THE INVENTION

This invention pertains to a method for determining the swelling-clay content in shales and shaly sandstones by high-frequency dielectric constant measurements.

BACKGROUND OF THE INVENTION

The determination of the swelling-clay content, especially smectite content, of a formation is important in both the exploration for and the production of hydrocarbons. In exploration, the clay content is useful in the determination of water and hydrocarbon saturations in shaly reservoir formations. During drilling, knowledge of the swelling-clay content is useful in making a determination of the amount of potassium which needs to be added to drilling muds in order to provide wellbore stability. The swelling-clay content also provides information regarding drilling problems such as wellbore instability, stuck pipe, bottom-hole fill, bit balling, mud rings, torque, drag, and solids build-up in the drilling fluid. Completion problems such as formation damage in shaly sands, logging and coring failures, hole washouts, and poor cement jobs sometimes attributable to the excessive clay content of the formation. It is desirable, therefore, to be able to obtain, at the wellsite, timely estimates of the swelling-clay content of earth formations.

Two of the most common methods for determining the swelling-clay content of a sample are the surface area method and the cation exchange capacity (CEC) method. Both of these methods are well established in the art. Briefly, the surface area method correlates the weight increase of a sample exposed to ethylene glycol, ethylene glycol monoethyl ether (EGME), or a similar fluid to the swelling-clay content. See for example, Theng, B. K. G., "The Chemistry of Clay Organic Reactions", John Wiley & Sons, New York, 1974, Chapter 3, for a brief summary of surface area methods used in determining swelling-clay content. The CEC method, on the other hand, correlates the number of exchangeable cations in a sample (cations in the sample that can be replaced by another cation such as barium or ammonium) to the swelling-clay content. See for example, Van Olphen, H., "An Introduction to Clay Colloid Chemistry", Wiley-Interscience, New York, 1977, Chapter 5, for a brief summary of CEC methods used in determining swelling-clay content. However, it is also well established that both of these methods usually require days to complete and cannot easily be done at the wellsite. In addition, these methods can be affected by the presence of other, nonswelling clay minerals, such as zeolites and amorphous silica, and can be sensitive to experimental techniques.

There exists a need, therefore, for a rapid and reliable wellsite method for the determination of the swelling-clay content in shales and shaly formations.

Currently, dielectric measurements are utilized for other, unrelated purposes. For example, dielectric measurements are utilized in logging tools for making determinations of the water and hydrocarbon content in sandstones and carbonates. These logging tools are not designed for making swelling-clay determinations. In addition, these logging tools lose their effectiveness in high-salinity formations.

To the best of Applicants' knowledge, dielectric measurements are not used for making determinations of swelling-clay content. In fact, current art actually dismisses dielectric responses observed between 1–50 MHz in dilute aqueous swelling-clay suspensions as anomalies which vanish with increasing salinity. See for example, Raythatha, R. and Sen, P. N., "Dielectric Properties of Clay Suspensions in the MHz to GHz Range", *Journal of Colloid and Interface Science*, February 1986, Vol. 109, No. 2, in general, and particularly see pages 305 and 308 wherein it is stated that the electrochemical effects (of swelling-clays) become unimportant at high salinities and the geometrical effects dominate. Therefore, the prior art fails to recognize that dielectric measurements may be utilized for making determinations of the swelling-clay content in shaly formations.

SUMMARY OF THE INVENTION

The present invention presents a method for rapidly determining at the wellsite the swelling-clay content in shales and shaly sandstones. The invention describes a method for determining the swelling-clay content of shales and shaly sandstones by high-frequency dielectric measurements (for purposes of this application frequencies greater than 0.1 MHz are deemed "high frequency") which includes: grinding a dried rock sample to a size suitable for testing (preferably, the sample should be able to pass sieve sizes from 0.01 to 1.00 millimeter); washing the rock sample with a fluid having a water activity substantially less than that of water (using the dielectric constant as a measure of water activity, the dielectric constant of the fluid should be between 5 and 80) and which may contain a soluble cation (the soluble cations that may be added comprise: $Li^+$, $Na^+$, $K^+$, $Rb^+$, $Cs^+$, $(NH_4)^+$, $Mg^{+2}$, $Ca^{+2}$, $Ba^{+2}$, $Sr^{+2}$, $Co^{+2}$, $Ni^{+2}$, $Cu^{+2}$, $Zn^{+2}$, $La^{+3}$, $Fe^{+3}$, $Cr^{+3}$, $Al^{+3}$, or other similar cations); packing the washed rock sample into a sample cell suitable for dielectric measurement; measuring the dielectric constant at a preselected frequency to allow uniform comparison of rock samples (the frequency should be between 0.1 and 100 MHz); and comparing the measured dielectric constant of the rock sample to a calibration curve derived from samples of known swelling-clay content whose dielectric constants were measured in the same manner.

A determination of the swelling-clay content may be performed at different levels depending on the nature of the sample to be compared. Briefly, these different levels of determination differ in the washing procedures used in the practice of this invention.

It is an advantage of this invention that it can determine at wellsites in a timely manner the swelling-clay content of a formation.

DETAILED DESCRIPTION OF THE PREFERRED EMBODIMENT

Figure 1:
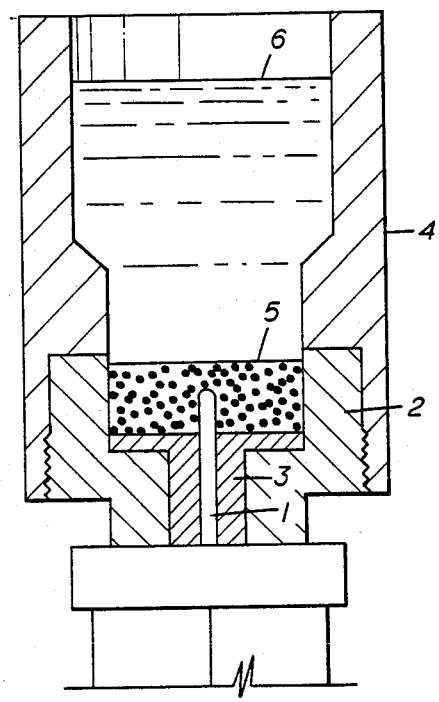
FIG. 1 schematically illustrates a sample cell suitable for dielectric constant measurements.

The present invention concerns a timely wellsite method for determining the swelling-clay content of shales and shaly sandstones. The principal steps in the preferred embodiment of this method include: grinding a dried rock sample to a predetermined size suitable for testing to allow uniform comparison of rock samples; washing the rock sample with a fluid, which may contain a soluble cation, having a water activity substantially less than that of bulk water; packing the washed rock sample into a sample cell suitable for dielectric measurements; measuring the dielectric constant at a preselected frequency to allow uniform comparison of rock samples, and comparing the measured dielectric constant of the rock sample to a calibration curve derived from samples of known swelling-clay content whose dielectric constants have been determined in substantially the same manner.

The invention will now be described in greater detail with reference to the accompanying drawings.

A sample from a formation is dried sufficiently so that it can be ground to a predetermined size. This size is neither so small that there is difficulty grinding high-clay-content samples nor so large that there is difficulty packing the sample in a measuring cell. For practical field testings, the sample should pass sieve sizes ranging from about 0.01 millimeter to 1.0 millimeter. A preferred sieve size is 0.12 millimeter because this size is a standard sieve size which is available with commonly available grinders.

The rock sample is then washed with a fluid having a water activity substantially less than that of water. Using the dielectric constant as a measure of water activity, the fluid's dielectric constant should range between about 5 and 80. This fluid attenuates the swelling behavior of rock samples containing large amounts of swelling-clays such that it will permit subsequent sample treatment and measurement. A fluid suitable for this purpose is an alcohol-water mixture. A suitable alcohol-water mixture which is commonly available is rubbing alcohol (70% isopropyl alcohol and 30% water by volume). The dielectric constant of this alcohol-water mixture is 35, which corresponds to a suitable water activity level.

In a typical measuring routine, 200 milligrams of a dried, ground formation sample are placed in a standard 7 millimeter test tube. The test tube is nearly filled with the fluid (for example, the alcohol-water mixture). The sample and fluid are then agitated or "vortexed" to provide satisfactory mixing of the fluid and sample. The test tube is then allowed to sit for a period suitable for the solvation, or hydration, of the swelling clay. This period of time may vary with experimental techniques. However, all samples which will be compared should sit for approximately the same periods of time. In our experience, a period of about two hours will provide sufficient time for the solvation, or hydration, of the swelling clay. Ultimately, the washing step with the alcohol-water mixture should permit the solvation, or hydration, of even the least-swellable clays, such as kaolinite, as well as allow the subsequent centrifuging (at a relatively low rate without making necessary the addition of salts to promote flocculation) of the most-swellable clays, such as bentonite.

In the preferred embodiment of the invention, four levels of swelling-clay determination are possible. These levels of determination alter the procedure utilized at the washing step.

The first, or narrowest, level of determination may be used when only the swelling-clay content of samples from a single site are to be determined (for example, a site in the Gulf of Mexico). No cations need to be added to the fluid at this first level of determination. The second level of determination may be used when comparisons between different sites in a region, which contain similar rock matrices, are required (for example, all North Sea sites, which are predominantly sandstone rock, or all Saudi Arabian sites, which are predominantly carbonate rock). The third level of determination may be used when comparisons between different regions, which contain different rock matrices, are required (for example, some North Sea samples and some Saudi Arabian samples). The fourth, or broadest, level of determination may be used when comparisons between different regions of varying rock matrices are required and the swelling clays are known to be interstratified with illite clays.

The four different levels of determination will now be described in greater detail.

The first, or narrowest, level of determination requires that the sample be first washed with a fluid containing no cations. This step has already been described above.

The second level of determination requires that the sample be washed with a fluid to which sodium chloride has been added. A preferred concentration is 31.7 grams of sodium chloride per liter of fluid. Sodium cations are exchanged with all exchangeable cations in the sample and places all swelling clays in their most swellable state. Naturally occurring swelling clays, such as montmorillonite, may contain either sodium, calcium, potassium, or magnesium as exchangeable cations, or any combination of the four. The sodium exchange therefore standardizes the samples from different sites. This example utilizes sodium as the exchangeable cation. However, it is emphasized that other cations may be utilized in place of sodium to standardize the interlayer cation. Such other cations are: $Li^+$, $K^+$, $Rb^+$, $Cs^+$, $(NH_4)^+$, $Mg^{+2}$, $Ca^{+2}$, $Ba^{+2}$, $Sr^{+2}$, $Co^{+2}$, $Ni^{+2}$, $Cu^{+2}$, $Zn^{+2}$, $La^{+3}$, $Fe^{+3}$, $Cr^{+3}$, $Al^{+3}$. For this second level of determination non-swelling state cations as well as swelling-state cations may be utilized.

The third level of determination requires an additional, separate washing. In addition to washing a first portion of the sample using the sodium chloride-containing fluid, as the swelling state inducing cation, a second portion of the sample is washed with a lanthanum chloride-containing fluid, as the non-swelling state inducing cation, in order to make two separate cation exchanges. The lanthanum cation is exchanged with all exchangeable cations in the sample and places the swelling-clays in that sample in a nonswelling state. Ultimately, the difference between the dielectric constants of the sodium-exchanged sample portion and the lanthanum-exchanged sample portion is measured. Thus, background fluctuations due to the presence in the sample of varying amounts of nonexchangeable quartz, carbonates, and other nonswelling minerals is eliminated. A preferred concentration for the lanthanum-exchanged sample is 66.6 grams of lanthanum chloride per liter of fluid. This example utilizes sodium as the swelling state inducing cation. It is emphasized that any other swelling state inducing cation may be utilized in place of sodium to obtain similar results. Such other swelling state inducing cation may be any of the following: $Li^+$, $Ca^{+2}$, $Sr^{+2}$, or $Ba^{+2}$. In addition, this example utilized lanthanum as the non-swelling state inducing cation. Again, it is emphasized that any other non-swelling state inducing cation may be utilized in place of lanthanum to obtain similar results. Such other non-swelling state inducing cation may be any of the following: $Cs^+$, $Rb^+$, $La^{+3}$, $Cr^{+3}$, $Al^{+3}$, or $Fe^{+3}$.

The fourth, or broadest, level of determination also requires two separate washings. In addition to washing a first portion of the sample using the sodium chloride-containing fluid as the swelling state inducing cation (any other swelling state cation may be utilized), a second portion of the sample is washed with a potassium chloride-containing fluid in order to make two separate cation exchanges. Illite, interstratified with swelling clays, is relatively nonswelling and contains potassium as the interlayer cation. The illitic potassiums are relatively nonexchangeable and the potassium exchange therefore gives a measure of the illite/smectite nature of the swelling-clay. Ultimately, the fourth level of determination is a comparison involving the dielectric measurements of the two portions of the sample that provides the measure of the swelling-clay content. A preferred concentration for the potassium chloride-exchanged sample is 35.9 grams of potassium chloride per liter of fluid. This example utilizes potassium as the illitic state inducing cation. Any other illitic state inducing cation may be utilized in place of potassium to obtain the desired results. An example of another illitic state inducing cation is $NH_4^+$.

Samples which have been washed with cation-containing fluids, for example sodium chloride, lanthanum chloride, or potassium chloride, are then washed with the non-cation-containing fluid, such as the rubbing alcohol, until the conductivity of the decantate is no more than twice that of the washing fluid in its original state (without the addition of salts). This level of conductivity represents the effective removal of excess exchanged cations from the washing fluid.

Subsequent to the washing step, the sample is packed into a sample cell suitable for dielectric constant measurements, such as the sample cell illustrated in FIG. 1. The use of coaxial sample cells for dielectric measurements at frequencies above 0.1 MHz are well established in the art. The coaxial design for the sample cell is used because of the ease of adding the slurry to the cell and because of the ease of packing the sample into the cell around the inner coaxial conductor by centrifuge methods. As shown in FIG. 1, a suitable sample cell is of a coaxial geometry, consisting of a center conductor 1 and an outer conductor 2 separated by a teflon spacer 3. A plastic jacket 4 has been attached to the outer conductor 2. The rock sample 5 and fluid 6 are added to the cavity of the sample cell. When the rock sample 5 has been packed into the sample cell, the rock sample 5 resides between the center conductor 1 and outer conductor 2, above the teflon spacer 3, and completely covers the center conductor 1. The fluid 6 is contained above the rock sample 5 and is contained within the plastic jacket 4.

In order to transfer the washed sample to this sample cell, portions of the non-cation-containing fluid are added to the sample. The sample and fluid are vortexed to provide satisfactory mixing, and the slurry is transferred into the sample cell.

The slurry-filled sample cell is then centrifuged for packing the sample in the sample cell. For example, centrifuging the sample at a rate of 1800 revolutions per minute for one minute uniformly packs the sample between the inner and outer conductors of the coaxial sample cell leaving the fluid in the plastic jacket above the measuring portion of the sample cell. This centrifuging rate is suggested because it is a moderate rate for small, portable centrifuges and because the rate and duration are sufficient to adequately pack bentonite into the sample cell.

The sample cell is then attached to a capacitance meter operating at a set frequency. Capacitance meters are well known in the art and are commonly available. A suitable test frequency is 1 MHz. A frequency of 1 MHz is sufficiently high to avoid electrode-polarization effects which distort measurements at lower frequencies and is sufficiently low to quantify the magnitude of the swelling-clay dielectric response. This dielectric response originates within the interlayer region of the swelling clay. This response occurs due to the reduced mobility of the interlayer exchangeable cations (for example, $Na^+$ or $La^{+3}$).

The sample's capacitance is measured and converted to the dielectric constant by well established methods. Briefly, the capacitances of two standards placed in the cell may be measured (for example, air whose dielectric constant is 1 and distilled water whose dielectric constant is 78 at a temperature of 25° C.) A linear relationship may then be established between the measured capacitance and the dielectric constant.

Depending upon the level of determination desired, comparisons to other samples of known dielectric constant and swelling-clay content are made to determine the swelling-clay content of the sample being tested.

The first, or narrowest, level of determination compares the dielectric constant of the non-cation-washed sample to a calibration curve derived from samples of known swelling-clay content whose dielectric constants were determined in the same manner as the sample. Such a calibration curve is illustrated in FIG. 2.

Figure 2:
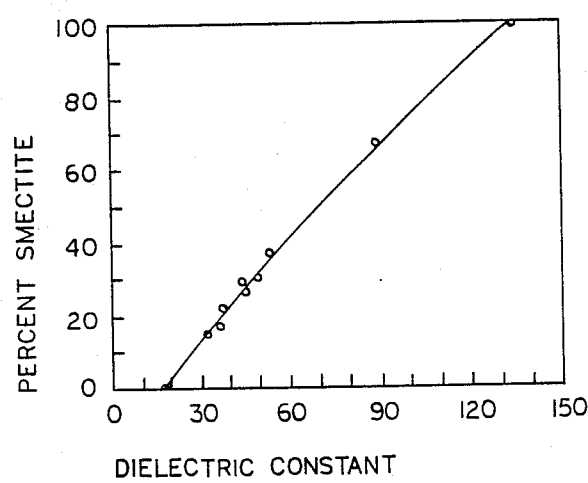
FIG. 2 is a Percent Smectite-Dielectric Constant diagram for smectite (montmorillonite)/quartz mixtures showing the correlation between the dielectric constant and the percent smectite (swelling-clay content) for the first, or narrowest, level of swelling-clay determination.

FIG. 2 illustrates the relationship of the dielectric constant to the swelling-clay content obtained from samples containing montmorillonite/quartz mixtures. FIG. 2 depicts the swelling-clay content of the sample as the percent smectite by weight. FIG. 2 depicts a correlation between the dielectric constant and percent smectite, which may also be expressed by the following empirical correlation: $Y = 2.45 X^{0.8} - 23.6$; where X is the dielectric constant and Y represents the percent smectite.

The second level of determination compares the dielectric constant of the sodium-washed sample to a calibration curve derived from samples of known swelling-clay content whose dielectric constants were determined in the same manner as the sample. Such a calibration curve is illustrated in FIG. 3.0.

Figure 3:
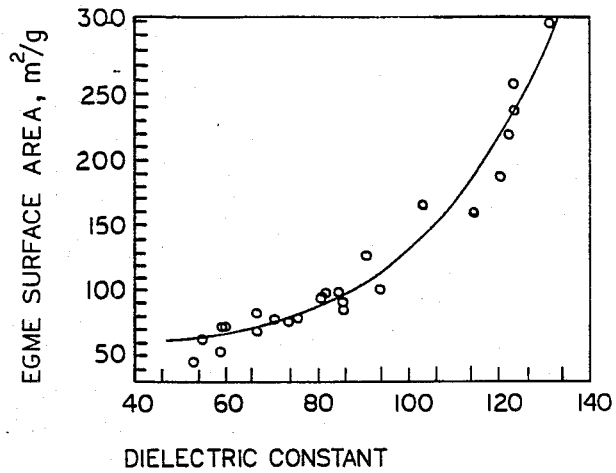
FIG. 3 is an EGME Surface Area-Dielectric Constant diagram for North Sea cuttings showing the correlation between the dielectric constant and the EGME surface area (swelling-clay content) for the second level of swelling-clay determination.

FIG. 3 depicts the swelling-clay content of the sample as an EGME surface area measurement. It is well established in the art that swelling-clay content is expressed as an indirect measurement. For example, the swelling-clay content of a sample may be expressed in terms of its EGME surface area or, alternatively, it may be expressed in terms of the cation-exchange capacity of the sample. The manner of expressing swelling-clay content varies with laboratory methods, none of which provide an absolute measurement of swelling-clay content of field cuttings. In other words, the measurement of the swelling-clay content is a relative measurement made against an established standard. It is to be understood that the EGME standard has been chosen in FIGS. 3, 4, and 5 for purposes of illustrating the invention and not by way of limitation, as this invention may be practiced in connection with any other method of making the relative determination of swelling-clay content.

FIG. 3 depicts a correlation between the sodium-exchanged dielectric constant and the EGME surface area for North Sea cuttings, which may also be expressed by the following empirical correlation: $Y = 1.74 \times 10^{-7} X^{4.3} + 58.7$; where X is the dielectric constant and Y is the EGME surface area expressed in $m^2/g$.

The third level compares the dielectric constant difference of the sodium-washed sample's dielectric constant and the lanthanum-washed sample's dielectric constant to a curve derived from samples of known swelling-clay content whose dielectric constants and dielectric differences were determined in the same manner as the sample. Such a calibration curve is illustrated in FIG. 4.0.

Figure 4:
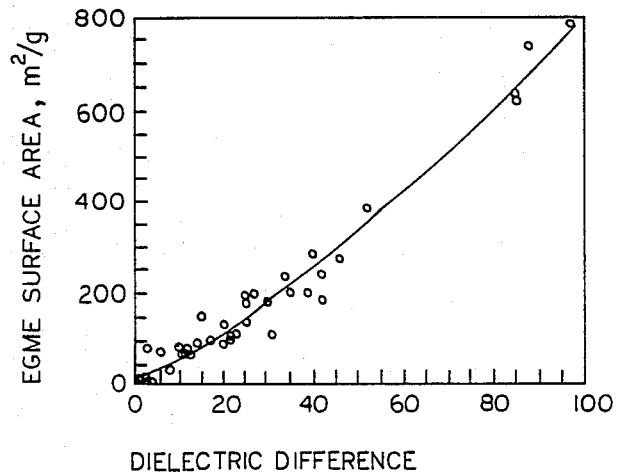
FIG. 4 is an EGME Surface Area-Dielectric Constant Difference diagram for worldwide samples showing the correlation between the dielectric constant difference and the EGME surface area (swelling-clay content) for the third level of swelling-clay determination.

FIG. 4 depicts a correlation between the difference between the dielectric constant of the sodium exchange portion and the lanthanum exchange portion and the EGME surface area for a selection of samples from various regions of the world. This correlation may be also expressed by the following empirical formula: $Y = 1.96 X^{1.3} + 18.2$; where X is the difference in dielectric constant and Y is the EGME surface area expressed in $m^2/g$.

The fourth, or broadest, level compares the dielectric constant of the sodium-washed sample and the sample's dielectric ratio determined by the sodium-potassium dielectric difference divided by the sodium-washed sample's dielectric constant to a family of curves, each depicting a dielectric region, whose dielectric constants and dielectric ratios were determined in the same manner as the sample. Such a family of calibration curves is illustrated in FIG. 5.

Figure 5:
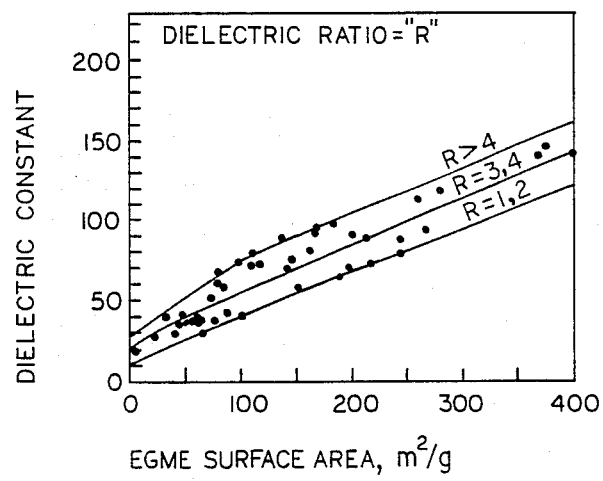
FIG. 5 is an EGME Surface Area-Dielectric Constant diagram for worldwide samples showing the correlation between the dielectric constant regions (or bands) and the EGME surface area (swelling-clay content) for the fourth, or broadest, level of swelling-clay determination.

FIG. 5 depicts a correlation between the sodium-exchanged dielectric constant and the EGME surface area for a selection of samples from various regions of the world. Some of these samples contain swelling clay interstratified with illite. The dielectric regions, or bands, have been developed by assigning each sample a dielectric ratio value determined by the following formula: $Y = INT(10 \times (W-X)/W)$; where W is the dielectric constant of the sodium-exchanged portion, X is the dielectric constant of the potassium-exchanged portion, Y is the dielectric ratio, and INT indicates that the integer (i.e. whole number) value is to be used, rather than a fractional calculated value.

It is emphasized that FIGS. 2 through 5 are merely examples of the correlations which may be obtained to determine the swelling-clay content of formations using the invention. It is to be understood that many other similar correlations and diagrams may be created using the invention to obtain the swelling-clay content of samples.

The above description and examples of the invention are offered only for the purpose of illustration, and it is not intended that the invention be limited except by the scope of the appended claims.

We claim:

1. A method for measuring the swelling-clay content of earth formations by dielectric measurements, comprising the steps of:
   (a) grinding a sample of the earth formation to a size suitable for testing;
   (b) washing the sample with a fluid having a water activity substantially less than that of water;
   (c) packing the washed sample into a sample cell suitable for dielectric measurement;
   (d) measuring the dielectric constant of the washed sample at a preselected frequency; and
   (e) comparing the measured dielectric constant of the rock sample to a calibration curve, to determine the swelling-clay content of the earth formation.

2. The method of claim 1, further including the step of repeating steps a through e for further samples whose swelling-clay contents are to be measured.

3. The method of claim 1 wherein said fluid is a mixture of alcohol and water.

4. The method of claim 3 wherein said mixture is 70% (volume) isopropyl alcohol and 30% (volume) water.

5. The method of claim 1 wherein said packing is accomplished by centrifuging the sample cell.

6. The method of claim 1 wherein the preselected frequency of measurement is about 1 megahertz.

7. A method for measuring the swelling-clay content of shales and shaly sandstone formations by high-frequency dielectric measurements, comprising the steps of:
   (a) grinding a sample of a formation to a predetermined size suitable for testing;
   (b) washing the sample with a fluid having a water activity substantially less than that of water;
   (c) packing the washed sample into a sample cell suitable for dielectric measurement;
   (d) measuring the dielectric constant of the washed sample at a preselected frequency to allow uniform comparison with other samples; and
   (e) comparing the measured dielectric constant of the sample to a calibration curve derived from samples of known dielectric constant and swelling-clay content, to determine the swelling clay content of the formation.

8. The method of claim 7, further including the step of repeating steps a through e for each sample to be compared.

9. The method of claim 7 wherein said fluid is a mixture of alcohol and water.

10. The method of claim 9 wherein said mixture is 70% (volume) isopropyl alcohol and 30% (volume) water.

11. The method of claim 7 wherein said packing is accomplished by centrifuging the sample cell.

12. The method of claim 7 wherein the preselected frequency of measurement is about 1 megahertz.

13. A method for measuring the swelling-clay content of shales and shaly sandstone formations by high-frequency dielectric measurements, comprising the steps of:
   (a) grinding a sample of a formation to a predetermined size suitable for testing;
   (b) washing the sample with a fluid having a water activity substantially less than that of water to which a cation has been added;
   (c) packing the washed sample into a sample cell suitable for dielectric measurement;
   (d) measuring the dielectric constant of the washed sample at a preselected frequency to allow uniform comparison with other samples; and
   (e) comparing the measured dielectric constant of the sample to a calibration curve derived from samples of known dielectric constant and swelling-clay content, to determine the swelling-clay content of the formation.

14. The method of claim 13 wherein said cation comprises $Li^+$, $Na^+$, $K^+$, $Rb^+$, $Cs^+$, $(NH_4)^+$, $Mg^{+2}$, $Ca^{+2}$, $Ba^{+2}$, $Sr^{+2}$, $Co^{+2}$, $Ni^{+2}$, $Cu^{+2}$, $Zn^{+2}$, $La^{+3}$, $Fe^{+3}$, $Cr^{+3}$, or $Al^{+3}$.

15. The method of claim 13 wherein said fluid is a mixture of alcohol and water.

16. The method of claim 15 wherein said mixture is 70% (volume) isopropyl alcohol and 30% (volume) water.

17. The method of claim 13 wherein said packing is accomplished by centrifuging the sample cell.

18. The method of claim 13 wherein the preselected frequency of measurement is about 1 megahertz.

19. The method of claim 13, further including the step of repeating steps a through e for each sample to be compared.

20. A method for measuring the swelling-clay content of shales and shaly sandstone formations by high-frequency dielectric measurements, comprising the steps of:
   (a) grinding a sample of a formation to a predetermined size suitable for testing;
   (b) washing a first half of said sample with a fluid having a water activity substantially less than that of water to which a swelling state inducing cation has been added;
   (c) washing a second half of said sample with a fluid having a water activity substantially less than that of water to which a non-swelling state inducing cation has been added;
   (d) packing said first half of said washed sample in a first sample cell suitable for dielectric measurement;
   (e) packing said second half of said washed sample in a second sample cell suitable for dielectric measurement;
   (f) measuring the dielectric constant of said first half of said sample at a preselected frequency to allow uniform comparison with other samples;
   (g) measuring the dielectric constant of said second half of said sample at said preselected frequency;
   (h) subtracting the measured dielectric constant of said second sample from the measured dielectric constant of said first sample and obtaining the dielectric difference; and
   (i) comparing the measuring dielectric difference to a calibration curve derived from samples of known dielectric difference and swelling-clay content, to determine the swelling-clay content of the formation.

21. The method of claim 20 wherein said swelling state inducing cation comprises $Na^+$, $Li^+$, $Ca^{+2}$, $Sr^{+2}$, or $Ba^{+2}$.

22. The method of claim 20 wherein said non-swelling state inducing cation comprises $Cs^+$, $Rb^+$, $La^{+3}$, $Cr^{+3}$, $Al^{+3}$, or $Fe^{+3}$.

23. The method of claim 20, further including the step of repeating steps a through i for each sample to be compared.

24. The method of claim 20 wherein said packing is accomplished by centrifuging the sample cell.

25. The method of claim 20 wherein the preselected frequency of measurement is about 1 megahertz.

26. The method of claim 20 wherein said fluid is a mixture of alcohol and water.

27. The method of claim 26 wherein said mixture is 70% (volume) isopropyl alcohol and 30% (volume) water.

28. A method for measuring the swelling-clay content of earth formations by dielectric measurements, comprising the steps of:
   (a) grinding a sample of the earth formation to a size suitable for testing;
   (b) washing a first half of said sample with a fluid having a water activity substantially less than that of water to which a swelling state inducing cation has been added;
   (c) washing a second half of said sample with a fluid having a water activity substantially less than that of water to which an illitic state inducing cation has been added;
   (d) packing said first half of said washed sample in a sample cell suitable for dielectric measurement;
   (e) packing said second half of said washed sample in a sample cell suitable for dielectric measurement;
   (f) measuring the dielectric constant of said first half of said sample at a preselected frequency;
   (g) measuring the dielectric constant of said second half of said sample at said preselected frequency;
   (h) obtaining the dielectric ration by dividing the difference between the measured dielectric constant of said first half of said sample and the measured dielectric constant of said second half of said sample by the dielectric constant of said first half of said sample; and
   (i) comparing the measured dielectric constant of said first half of said sample obtained in step f and the dielectric ratio obtained in step h to calibration curves, to determine the swelling-clay content of the earth formation.

29. The method of claim 28 wherein said swelling state inducing cation comprises $Na^+$, $Li^+$, $Ca^{+2}$, $Sr^{+2}$, or $Ba^{+2}$.

30. The method of claim 28 wherein said illitic state inducing cation comprises $K^+$ or $NH_4^+$.

31. The method of claim 28, further including the step of repeating steps a through i for each sample to be compared.

32. The method of claim 28 wherein said packing is accomplished by centrifuging the sample cell.

33. The method of claim 28 wherein the preselected frequency of measurement is about 1 megahertz.

34. The method of claim 28 wherein said fluid is a mixture of alcohol and water.

35. The method of claim 34 wherein said mixture is 70% (volume) isopropyl alcohol and 30% (volume) water.

36. A method for measuring the swelling-clay content of shales and shaly sandstone formations by high-frequency dielectric measurements, comprising the steps of:
 (a) grinding a sample of a formation to a predetermined size suitable for testing;
 (b) washing a first half of said sample with a fluid having a water activity substantially less than water to which a swelling state inducing cation has been added;
 (c) washing a second half of said sample with a fluid having a water activity substantially less than water to which an illitic state inducing cation has been added;
 (d) packing said first half of washed sample in a sample cell suitable for dielectric measurement;
 (e) packing said second half of said washed sample in a sample cell suitable for dielectric measurement;
 (f) measuring the dielectric constant of said first half of said sample at a preselected frequency to allow uniform comparison with other rock samples;
 (g) measuring the dielectric constant of said second half of said sample at said preselected frequency;
 (h) obtaining the dielectric ratio by dividing the difference between the measured dielectric constant of said first half of said sample and the measured dielectric constant of said second half of said sample by the dielectric constant of said first half of said sample; and
 (i) comparing the measured dielectric constant of said first half of said sample obtained in step f and the dielectric ratio obtained in step h to calibration curves derived from samples of known dielectric constants, dielectric ratios, and swelling-clay content, to determine the swelling-clay content of the earth formation.

37. The method of claim 36 wherein said swelling state inducing cation comprises $Na^+$, $Li^+$, $Ca^{+2}$, $Sr^{+2}$, or $Ba^{+2}$.

38. The method of claim 36 wherein said illitic state inducing cation comprises $K^+$ or $NH_4^+$.

39. The method of claim 36, further including the step of repeating steps a through i for each sample to be compared.

40. The method of claim 36 wherein said packing is accomplished by centrifuging the sample cell.

41. The method of claim 36 wherein the preselected frequency of measurement is about 1 megahertz.

42. The method of claim 36 wherein said fluid is a mixture of alcohol and water.

43. The method of claim 42 wherein said mixture is 70% (volume) isopropyl alcohol and 30% (volume) water.

* * * * *